(12) United States Patent
Teeter, Jr.

(10) Patent No.: US 7,794,548 B2
(45) Date of Patent: Sep. 14, 2010

(54) ETHANOL PROCESS USING PRE-FERMENTATION SOLIDS REMOVAL

(75) Inventor: Floyd C. Teeter, Jr., Woodbury, MN (US)

(73) Assignee: Crown Iron Works Company, Roseville, MN (US)

( * ) Notice: Subject to any disclaimer, the term of this patent is extended or adjusted under 35 U.S.C. 154(b) by 670 days.

(21) Appl. No.: 11/744,688

(22) Filed: May 4, 2007

(65) Prior Publication Data

US 2007/0269873 A1 Nov. 22, 2007

Related U.S. Application Data

(60) Provisional application No. 60/797,532, filed on May 4, 2006.

(51) Int. Cl.
- *C08B 30/02* (2006.01)
- *C08B 30/04* (2006.01)
- *C12P 7/06* (2006.01)

(52) U.S. Cl. .......................................... 127/67; 435/161

(58) Field of Classification Search .................... 127/67; 435/161

See application file for complete search history.

(56) References Cited

U.S. PATENT DOCUMENTS

| | | | | |
|---|---|---|---|---|
| 4,769,112 A | | 9/1988 | Wheldon | 203/19 |
| 5,773,076 A | | 6/1998 | Liaw et al. | 426/656 |
| 5,851,301 A | * | 12/1998 | Robertson et al. | 127/67 |
| 5,968,585 A | | 10/1999 | Liaw et al. | 426/656 |
| 6,254,914 B1 | | 7/2001 | Singh et al. | 426/482 |
| 6,433,146 B1 | | 8/2002 | Cheryan | 530/373 |
| 6,899,910 B2 | | 5/2005 | Johnston et al. | 426/482 |
| 2002/0183490 A1 | | 12/2002 | Cheryan | 530/373 |
| 2005/0049400 A1 | | 3/2005 | Cheryan | 530/373 |
| 2007/0014905 A1 | * | 1/2007 | Chen et al. | 426/490 |

OTHER PUBLICATIONS

Iowa Corn, Distillers Grains/Ethanol Co-Products, http://www.iowacorn.org/ethanol_17.html; © 2006.
EXOL * The Ethanol Process—How Ethanol is Made; http://www.exolmn.com/process.htm; printed Jan. 4, 2006.
Iowa Corn, Frequently Asked Questions about DDGS, http://www.iowacorn.org/ethanol_12.html; © 2006.

* cited by examiner

*Primary Examiner*—Jon P Weber
*Assistant Examiner*—Kailash C Srivastava
(74) *Attorney, Agent, or Firm*—Nawrocki, Rooney & Silvertson, P.A.

(57) ABSTRACT

A process for preparing a starch-containing biomass particle stream having a significant percentage of fiber for processing into ethanol comprises the first step of: mixing the particle stream with a liquid solvent to dissolve at least a portion of the starch in the carbohydrate particle stream to form a carbohydrate slurry stream containing starch dissolved in the liquid solvent. This first step removes a portion of the fiber from the carbohydrate slurry stream. In a second step, the carbohydrate slurry stream is held in a settling tank to remove a further portion of the fiber. An enhancement to the process is suitable for use with shell corn or other biomass having an oil-containing germ portion and a non-germ portion comprising mainly carbohydrates and fiber. This enhancement includes the step of grinding the corn to particles of a size suitable for separating the germ particles from the non-germ particles. The germ particles are processed first to remove the oil and then to remove the carbohydrates.

12 Claims, 2 Drawing Sheets

ETHANOL PROCESS USING PRE-FERMENTATION SOLIDS REMOVAL

This is a regular application filed under 35 U.S.C. §111(a) claiming priority under 35 U.S.C. §119(e)(1), of provisional application Ser. No. 60/797,532, having a filing date of May 4, 2006.

TECHNICAL FIELD

The present invention relates to the production of ethanol from grain and other biomass, in particular from corn.

BACKGROUND OF THE INVENTION

One solution to the problem of dependence on foreign sources for energy, particularly for fuel for motor vehicles, is converting biomass to ethanol. The presently available processes use corn (maize) or other starch-containing biomass.

For efficiency, the process must convert a large percentage of the biomass to ethanol. The process should proceed rapidly so that the plant can produce the maximum amount of ethanol per unit time.

Corn is one preferred substance used for ethanol production. As is well known, corn kernels comprise a germ portion and a carbohydrate portion. The germ portion comprises about 8% of the entire weight. The germ contains about 40% by weight of valuable corn oil as well as some carbohydrates and fiber. The carbohydrate portion comprises starch, sugar, and fiber, and contains almost no oil. On a weight basis, corn kernels are about 6-7% oil, 60-70% carbohydrates, 20-25% fiber, and 10-12% water.

An efficient ethanol process uses enzymes to convert starches in the biomass to sugar before the fermentation. The process ferments sugars of any kind to produce $CO_2$ and the ethanol, but cannot convert starch to ethanol. Since $CO_2$ is a greenhouse gas, the less $CO_2$ produced, the better.

In current corn ethanol processes, corn is ground and mixed with a solvent to form a ground corn slurry. This slurry comprises both the germ and the carbohydrate portions. Enzymes added to the slurry convert the starch to sugar. Fermenting the sugar in the slurry then produces ethanol. A distillation step separates the ethanol from the slurry. The ethanol is then further refined to a form useable as automobile fuel.

The common ethanol production process has a number of problems. One is lack of efficiency. It turns out that the sum of all of the energy inputs needed to produce a unit measure of corn is not much less than the energy content of the ethanol provided by that unit measure. Of course, the ethanol process does produce some useful by-products, such as animal feed and the corn oil usable in plastic manufacture. But overall, current ethanol production processes are not outstandingly efficient.

Secondly, the current ethanol processes produces more contaminating fusel oil in the distilled ethanol than desirable. Fusel oil is an aromatic alcohol that reduces speed and efficiency in the distillation step. The fusel oil is a byproduct of corn oil that reaches the fermenting tank. Accordingly, removing as much corn oil as possible from the ground corn slurry reduces the concentration of the fusel oil.

BRIEF DESCRIPTION OF THE INVENTION

A process for preparing a starch-containing biomass particle stream having a significant percentage of fiber for processing into ethanol comprises a first step of: mixing the particle stream with a liquid solvent to dissolve at least a portion of the starch in the carbohydrate particle stream. This forms a carbohydrate slurry stream containing starch dissolved in the liquid solvent, and having a portion of the fiber removed. The solvent is typically an ethanol-water solution.

In a second step, holding the carbohydrate slurry stream in a settling tank for a time, allows a further portion of the fiber to settle to the bottom of the tank. Removing the upper portion of the material in the settling tank forms a liquid carbohydrate stream having only a small amount of fiber.

An enhancement to the process is suitable for use with shell corn or other biomass having an oil-containing germ portion and a non-germ portion comprising mainly carbohydrates and fiber. This enhancement includes the step of grinding the corn to particles of a size allowing separation of the germ particles from the non-germ particles. The germ particles are processed first to remove the oil and then to remove the carbohydrates.

In one embodiment, up-welling air lifts the lighter non-germ particles into a carbohydrate stream, and allows the germ particles to fall to form a germ stream.

DESCRIPTION OF THE PREFERRED EMBODIMENTS

Figure 1:
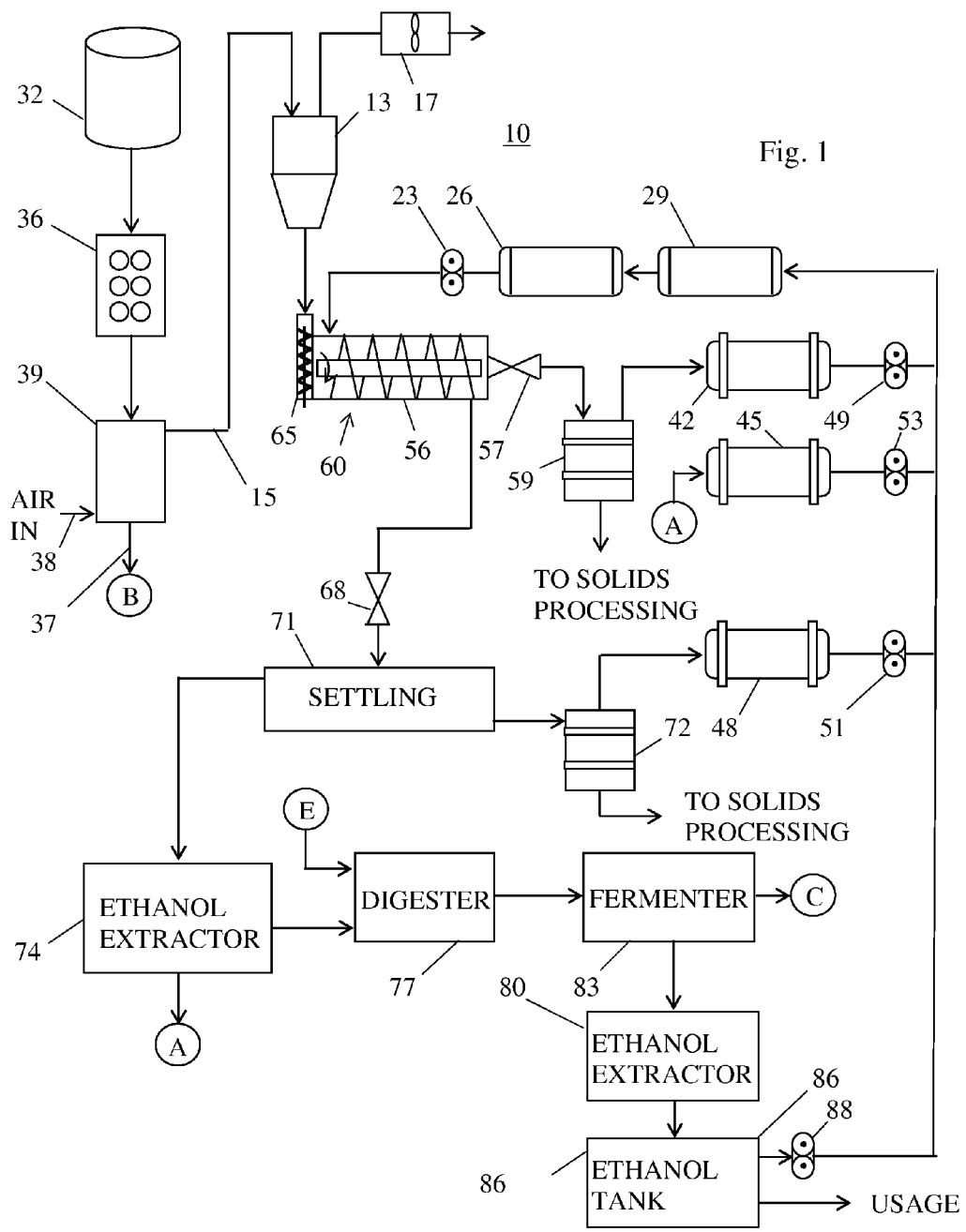
FIGS. 1 and 2 together form a block diagram of an ethanol production facility that incorporates the invention.
Figure 2:
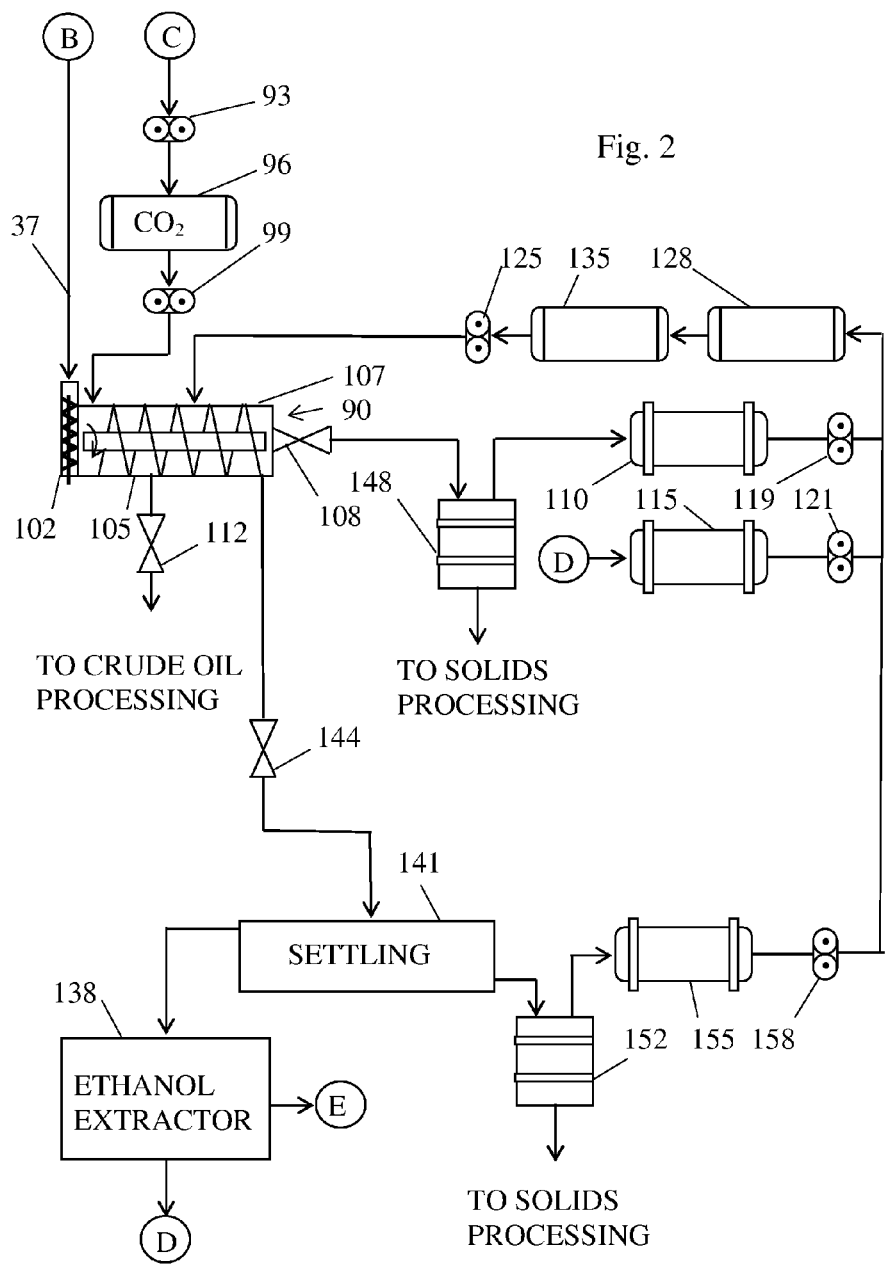

FIGS. 1 and 2 show a facility that uses a continuous flow process efficiently for producing ethanol and corn oil. The particular facility shown has front end and parallel process steps designed specifically for shell corn. Where non-corn starch-containing biomass is used, portions of the facility are suitable for converting this non-corn biomass into ethanol with efficiency that may be higher than currently achieved.

When corn is the biomass, corn oil is a valuable byproduct of this process. If biomass other than corn is used, one may omit the steps that separate the germ and non-germ portions of individual kernels, and that process the germ portion.

FIG. 1 shows the facility components that perform initial processing for partially separating the corn germ from the non-germ or starch and sugar (carbohydrate) portion, and that process the starch and sugar components of the shell corn. FIG. 2 shows the facility components that extract oil from the germ portion of the corn and process the remaining components of the germ portion for ethanol production.

Front End Corn Processing

In FIG. 1, loose kernel corn is stored in a bin 32. The kernel corn flows in a continuous stream to a mill or grinder 36. Ideally, mill 36 grinds the kernel corn to a fineness that creates individual particles that are either essentially all germ or are not germ. As mentioned, the germ is initially about 8% of the entire kernel. The particles comprising mainly germ material from the kernels have a slightly higher specific gravity than do non-germ particles.

Preferably individual particles exiting from mill 36 have a maximum dimension in the range of 0.3-0.6 mm. and a minimum dimensional range of perhaps half that range. This corresponds to a roller mill whose rollers are set to a 0.2-0.4 mm. spacing. For reasons to be explained, particles of this size are preferable.

The ground corn forms a stream of particles, hereafter "dry meal stream," that is delivered to a mechanical separator 39. In the version shown, separator 39 uses the different specific gravities of the particles in the dry meal stream to separate those with higher specific gravity containing the germ from those comprising only carbohydrate material. Preferably, separator 39 has an aspirator design that injects air at an air intake 38 near the bottom of separator 39. The air flows upwardly through corn particles falling into the top of and through separator 39.

Another version of mechanical separation relies on the characteristic of milled corn in which the germ portion particles are slightly larger than the non-germ portions.

For meal particles in the range mentioned, velocity of the upwelling air may be in the range of 50-150 fpm. A meal stream having particles in the upper end of the preferred size range will need slightly higher air velocity. Smaller particles will need lower air velocity. Experimentation suggests that too small particles will not allow the germ and non-germ particles to separate efficiently.

Separator 39 divides the corn meal stream into a carbohydrate stream and a germ stream. The carbohydrate stream exits the upper part of separator 39 and flows through a first duct or pipe 15 to a particle precipitator 13. The corn germ falls downwards through separator 39, flowing from the lower part of separator 39 as a germ stream into a second duct or pipe 37 and to an oil extractor 90, see FIG. 2. Connector element B symbolizes the continuation of duct 37 from FIG. 1 to FIG. 2.

The separation of the germ and the carbohydrate portions of the meal stream in the separator 39 is far from perfect. Typically, separator 39 approximately doubles the concentration of germ in the germ steam to around 15-20% from the approximately 8% by weight in the meal stream. Pure germ particles may comprise around 40% corn oil, so the concentration of corn oil in the germ stream may be approximately 6-8%. On the other hand, almost no germ particles flow into the carbohydrate stream. Hence little or no corn oil is present in the carbohydrate stream.

Carbohydrate Stream Processing

The velocity of the air flowing through duct 15 and carrying a higher proportion of slows as it enters precipitator 13. Particles suspended in the moving air fall toward the bottom of the precipitator 13 as the air slows within precipitator 13. In one version, a fan 17 connected at the top of precipitator 13 pulls air through a filter from precipitator 13. The vacuum that fan 17 creates in precipitator 13 is propagated to separator 39 through duct 15 causing air inflow through the air intake 38.

The carbohydrate stream falls into the intake 65 of a first auger-type carbohydrate extractor 60. The processing of the carbohydrate stream as it enters extractor 60 is suitable for a wide range of fementable biomass. Thus, sugar cane, sugar beets, and other sources of starch or sugar may be ground to a proper size of particles and provided to intake 65.

The intake 65 uses an auger to force the carbohydrate stream into a chamber 56 of extractor 60 maintained at relatively high pressure, perhaps 150-350 psi. The intake 65 includes an air seal or lock that retains pressure within chamber 56. A motor slowly rotates the extractor 60 auger to move the carbohydrate stream toward the outlet at the right end of chamber 56.

A pump 23 delivers a carbohydrate solvent, preferably an ethanol-water solution (also called a polar solvent), from a supply tank 26 maintained at a relatively high pressure, perhaps 3000-5000 psi., to the extractor chamber 56. The solvent sprays into the carbohydrate stream in chamber 56, and dissolves the carbohydrates in the carbohydrate stream to produce a liquid carbohydrate stream in the form of a thin slurry that flows through a throttling valve 68 to a settling tank 71. Current the preferred weight ratio of solvent flow rate to carbohydrate stream flow rate into chamber 56 is approximately 2:1, but ratios in the range of approximately 3:2 to 3:1 may also serve adequately.

Throttling valve 68 reduces to approximately atmospheric, the pressure of the liquid carbohydrate stream flowing from extractor 60 to settling tank 71. The liquid carbohydrate stream flowing to tank 71 has a substantial amount of particulate material comprising mainly fiber.

Settling tank 71 may be any of the drag link types that slowly stir and shift settling solids to an end of tank 71. Tank 71 has a port near the top through which fluid drains or decants as a liquid carbohydrate stream that flows into an ethanol extractor 74.

Solids that remain in chamber 56 of extractor 60 flow to a desolventizer unit 59 that vaporizes the ethanol-water solvent. The solvent vapors flow to a condenser 42 that condenses the solvent vapors. A throttling valve 57 forming a part of the condenser 42 reduces the pressure of the solvent vapors to approximately atmospheric in desolventizer 59. Pump 53 transports the condensed solvent to a processor 29. Pump 29 must produce pressure adequate to force the liquid solvent into the bottom of a tank 26 that may have solvent standing 30 m. or higher. Processor 29 represents components that rebalance the liquid water-ethanol solvent and supply it to tank 26 for reuse.

The solids flow from desolventizer 59 for further processing into animal feed. The processing to this point has removed most of the solvent from the solids.

In the settling tank 71, much of the particulate material in the liquid carbohydrate stream settles to the bottom where it flows out through a port near the bottom of tank 71 as a slurry stream to desolventizer 72.

Desolventizer unit 72 removes the ethanol from the slurry stream, which flows to condenser 48 and pump 51. From pump 51, the condensed ethanol flows to processor 29 for reuse. Where the composition of the slurry stream provided by the settling tank 71 is different from that provided by the desolventizer unit 59, the processing for the settling slurry in desolventizer unit 72 differs from that for the solids from the desolventizer unit 59. Where the composition of the solids exiting from tank 71 is similar to those that exit from extractor 60, the output of tank 71 may flow to desolventizer 59.

Extractor 74 vaporizes most of the ethanol remaining in the liquid carbohydrate stream. The solvent vapors flow through a pipe or duct as connector element A indicates, to a condenser 45 that condenses the ethanol vapors. Pump 53 brings the condensed ethanol vapors from condenser 45 to the input pressure of element 29, and supplies the condensed ethanol vapors to element 29. Extractor 74 may comprise several stages of ethanol removal employing distillation and other means as well. The industry well understands this ethanol extraction technology.

At this stage the liquid carbohydrate stream carries very little solid (fiber) material. The liquid carbohydrate stream flows to a digester 77 where enzymes mix with the liquid carbohydrate stream to convert starches in the liquid carbohydrate stream to sugar. Fermentation processes currently used cannot easily convert starch to ethanol. $CO_2$ is a normal byproduct of the fermentation process, and is provided by the piping indicated by connector element C to the oil removal portion of the process.

Digester 77, fermenter 83 and ethanol extractor 80 are conventional devices. However, removing nearly all of the fiber from the liquid carbohydrate stream prior to entering digester 77 as extractor 60 and settling tank 71 do, improves efficiency of the process substantially.

Ethanol from extractor 80 is stored in a tank 86 for distribution to users. Some of the ethanol in tank 86 flows to processor 29 through a pump 88 to replace ethanol lost in the extraction process. A suitable feedback system may control the amount of replacement ethanol provided to processor 29.

Oil Stream Processing

Mechanical separation of the germ and carbohydrate by separator 39 produces the germ stream carried in duct 37. Connector element B symbolizes the germ stream flow to an extractor 90 operating in a dual solvent mode.

The oil content of the germ stream is dissolved by liquid $CO_2$ provided by $CO_2$ tank 96. Preferably, the $CO_2$ in tank 96 is that fermenter 83 provides as a natural by-product of fermentation. Pump 93 receives the $CO_2$ from fermenter 83 through connector element C and compresses this $CO_2$ gas to liquefy the $CO_2$. A heat exchanger may be integral with pump 93 or tank 96 to cool the liquid $CO_2$, or even to allow the liquification to occur.

A pump 99 raises the pressure of the liquid $CO_2$ entering chamber 105 to a range of approximately 4000-8500 psi. The liquid $CO_2$ enters an oil extractor 90 at the upstream end of an extraction chamber 105.

Structurally, extractor 90 may be quite similar to carbohydrate extractor 60. However, extractor 90 operates in a dual mode that removes both oil and carbohydrates from the germ stream.

Extractor 90 has an intake 102 that receives the germ stream and forces this germ stream into an extraction chamber 105. The intake 102 includes an air seal or lock such as the auger shown, that retains pressure within chambers 105 and 107. Extractor 90 differs from extractor 60 because of the high pressure $CO_2$ intake at the upstream end of chamber 105.

Liquid $CO_2$ entering chamber 105 dissolves the corn oil in the germ stream material within chamber 105. Liquid $CO_2$ with dissolved oil flows from chamber 105 through a throttling valve 112 to conventional processing and storage elements. These elements remove the $CO_2$, perhaps by flashing off the $CO_2$, and refine the oil for use in food, plastics, and other industrial purposes.

The germ stream then flows to the downstream section of chamber 105 to remove much of the carbohydrate materials present in the germ stream. The downstream section of chamber 105 functions as an extractor in a manner very similar to that of extractor 60. An ethanol-water solution enters chamber 105 at a midway point and mixes with the germ stream.

The output at the downstream end of chamber 105 is very similar to that from extractor 60. Solids flow through throttling valve 108 to a desolventizer unit 148 similar to unit 59. Ethanol in these solids is vaporized and flows to condenser 110 and pump 119. Pump 119 pumps the condensed ethanol to a processor 128 and a storage tank 135 for reuse. Solids flow from unit 148 for further processing. It is easily possible that the ethanol vapors from extractor 90 have a compostion that allows desolventizer 59 to process them, in which case desolventizer 148, condenser unit 110, and pump 119 are unnecessary.

A liquid carbohydrate stream flows from chamber 105 through a throttling valve 144 to a second settling tank 141 similar to tank 71. The liquid stream from chamber 105 has a substantial percentage of carbohydrates and solids. Settling tank 141 is very similar to settling tank 71, and operates with very similar parameters. Tank 141 settles out much of the solid material in the liquid stream from extractor 90.

The solids that settle out in tank 141 flow from the bottom of tank 141 to desolventizer unit 152. The ethanol in the solids stream is vaporized and removed by desolventizer unit 152, condensed by condenser 155, and pumped up by pump 158 to the inlet pressure at processor 128.

A liquid comprising mainly carbohydrates flows from the top of the material in settling tank 141 to an ethanol extractor 138. Extractor 138 is similar to extractor 74 and removes most of the ethanol remaining in the liquid carbohydrate stream. The removed ethanol flows through connector element D to condenser 115 and pump 121 for reuse through processor 128.

The carbohydrate stream flows from extractor 138 through connector element E to the digester 77 on FIG. 1. In this way, the carbohydrate content of the germ portion can by used to produce ethanol without the undesirable effects of fusel oil within the fermenter 83. In addition, most of the fiber has been removed, which adds efficiency to the fermentation process.

The invention claimed is:

1. A process for treating a stream of dry corn kernels having therein a significant percentage of fiber, comprising the steps of:
    a) milling the corn kernels to form particles, some particles being germ particles that predominantly comprise germ material from the kernels and other particles being starch-containing particles that predominantly comprise starch material from the kernels;
    b) mechanically separating at least some of the germ particles from the starch-containing particles to form a germ particle stream with the remainder of the particles forming a starch-containing particle stream;
    c) mixing the starch-containing particle stream with a liquid solvent comprising a mixture of ethanol and water to dissolve at least a portion of the starch in the starch-containing particle stream to form a carbohydrate slurry stream containing (i) fiber and (ii) starch dissolved in the liquid solvent;
    d) transferring the carbohydrate slurry stream to a settling tank;
    e) holding the carbohydrate slurry stream in the settling tank for a time sufficient to allow settling of a portion of the fibers;
    f) removing the upper volume of the dissolved carbohydrate stream to form a reduced fiber liquid carbohydrate stream containing a smaller fraction of the fiber than did the original starch-containing particle stream; and
    g) thereafter, mixing an enzyme with the reduced fiber liquid carbohydrate stream to convert at least a portion of the starch in the reduced fiber liquid carbohydrate stream to sugars.

2. The process of claim 1, wherein the mechanical separation step comprises:
    a) transporting the milled kernel particles to a separator tank; and
    b) forcing air upwards through the milled kernel particles in the separator tank.

3. The process of claim 1, wherein the starch-containing particle stream-solvent mixing step includes the step of mixing the starch-containing particle stream with a liquid comprising a mixture of approximately 60-80% ethanol by weight.

4. The process of claim 1, including an evaporating step for removing a substantial percentage of the ethanol from the carbohydrate slurry stream.

5. The process of claim 1, including the steps of:
    a) fermenting the sugars in the reduced fiber liquid carbohydrate slurry stream produced by the enzyme-mixing step to produce ethanol; and b) mixing at least a portion of the ethanol formed by the fermentation step with the starch-containing biomass particle stream.

6. The process of claim 1, including the step of holding the carbohydrate slurry stream in the settling tank for at approximately 30 minutes to approximately 60 minutes.

7. The process of claim 1, wherein the step of mixing the starch-containing biomass carbohydrate particle stream with a liquid solvent occurs at a pressure substantially above atmospheric.

8. The process of claim 3, including evaporating at least a portion of any solvent in the carbohydrate slurry stream.

9. The process of claim 8, wherein the evaporating step includes removing a substantial percentage of the ethanol from the liquid carbohydrate stream, and further including the steps of:
   a) fermenting the liquid carbohydrate slurry stream to produce ethanol; and
   b) mixing at least a portion of the ethanol formed by the fermentation step with the starch-containing particle stream.

10. The process of claim 4, further including the steps of:
   a) fermenting the sugars in the reduced fiber liquid carbohydrate stream to produce ethanol and $CO_2$ gas;
   b) capturing the $CO_2$ gas and forming liquid $CO_2$ therefrom;
   c) mixing the liquid $CO_2$ with the germ particle stream to dissolve the germ particle stream's corn oil in the liquid $CO_2$ to form a dissolved corn oil stream;
   d) evaporating the liquid $CO_2$ from the dissolved corn oil stream to create a corn oil stream; and
   e) separating the corn oil stream to produce a germ particle carbohydrate stream with reduced corn oil.

11. The process of claim 10, including the steps of:
   a) mixing a carbohydrate solvent with the germ particle carbohydrate stream with reduced corn oil to form a germ particle carbohydrate slurry stream;
   b) mixing an enzyme with the germ particle carbohydrate slurry stream to convert at least a portion of the carbohydrate in the germ particle carbohydrate slurry stream to sugars; and
   c) fermenting the sugars in the germ particle carbohydrate stream to produce ethanol and $CO_2$ gas.

12. The process of claim 11, wherein the steps of mixing the liquid $CO_2$ with the germ particle stream and mixing a carbohydrate solvent with the germ particle stream occur in the same chamber.

* * * * *